United States Patent [19]

Lysfjord et al.

[11] 4,144,891

[45] Mar. 20, 1979

[54] HEART STIMULATOR LEAD SET

[75] Inventors: John P. Lysfjord, Minneapolis; James K. Byland, St. Paul, both of Minn.

[73] Assignee: Medtronic, Inc., Minneapolis, Minn.

[21] Appl. No.: 789,292

[22] Filed: Apr. 20, 1977

[51] Int. Cl.$^2$ .............................................. A61N 1/04
[52] U.S. Cl. ................................................. 128/419 P
[58] Field of Search .............. 128/418, 419 P, 419 PG

[56] References Cited

U.S. PATENT DOCUMENTS

| | | | |
|---|---|---|---|
| 3,253,595 | 5/1966 | Murphy, Jr. et al. | 128/418 |
| 3,593,718 | 7/1971 | Krasner | 128/419 PG |
| 3,760,332 | 9/1973 | Berkovits et al. | 128/418 |
| 3,804,098 | 4/1974 | Friedman | 128/419 P |
| 3,807,411 | 4/1974 | Harris et al. | 128/419 P |

OTHER PUBLICATIONS

Castillo et al., "Chest", vol. 59, No. 4, Apr. 1971, pp. 360–364.

*Primary Examiner*—William E. Kamm
*Attorney, Agent, or Firm*—R. Lewis Gable; Joseph F. Breimayer

[57] ABSTRACT

A set of heart stimulator leads including first and second leads is disclosed for respectively stimulating and sensing the atrium and ventricle of a patient's heart. The proximal end of each of the aforementioned first and second leads is associated with a heart pacemaker of the atrial-sensing, ventricular-inhibited (ASVIP) or sequential type, both of which have leads that are attached to the atria and ventricles. It is critical to ensure that the first and second leads associated respectively with the atrium and ventricle of the patient's heart, are not interchanged, which condition could possibly cause arrhythmias and morbidity, and is ensured by configuring the proximal end of each of the first and second leads so that both of these leads may not be inserted into the incorrect openings or bores of the pacemaker at the same time. In particular, the first or atrial lead has a portion adjacent to its proximal end of reduced dimension that permits its insertion into the corresponding first or atrial bore of the pacemaker, whereas the second or ventricle lead has a larger diameter at a corresponding portion adjacent the proximal end thereof corresponding to the dimension of the second or ventricular bore of the pacemaker, permitting insertion therein, but being greater than that of and thus not permitting insertion within the first or atrial bore of the pacemaker.

15 Claims, 5 Drawing Figures

HEART STIMULATOR LEAD SET

BACKGROUND OF THE INVENTION

1. Field of the Invention

This invention relates to electrical tissue stimulating devices and in particular to such a stimulator adapted to sense or to stimulate the atrium and to sense and stimulate the ventricle of a patient into which such a pulse generator would be inserted.

2. Description of the Prior Art

Implantable electrical medical tissue stimulating devices are well-known in the art. For example, one of the better-known tissue stimulators is the cardiac pacer, as shown, for example, in U.S. Pat. No. 3,057,356 to Wilson Greatbatch. These devices, such as the cardiac pacer, generally comprise a pulse generator further comprising a power source and associated electrical circuitry embedded in, and encapsulated in, or protected by a substance or substances substantially inert to body fluids and tissue. The electrical circuitry of the pulse generator is adapted to be connected by a lead or leads to one or more electrodes which are adapted to be placed adjacent to a remote, desired spot within the human body, such as adjacent to or within myocardial tissue. The cardiac pacer, for example, supplies electrical stimulating pulses to regulate cardiac function in the absence of naturally occurring cardiac pulses.

In implantation of pulse generator and lead, it is common practice for the surgeon to intravenously position or surgically attach the electrode at the distal end of the lead to the desired spot within the human body, that is, in or adjacent to myocardial tissue, and to connect thereafter the lead to a connector assembly associated with the electrical circuitry of the pulse generator in order to commence electrical stimulation of the heart tissue. Prior to making the electrical connection, the surgeon usually measures the electrical stimulation threshold level sufficient to maintain capture of the heart and the sensing threshold level sufficient to trigger the sense amplifier, if any, in the pulse generator circuitry to inhibit or appropriately trigger the generation of electrical stimulating pulses in the event the heart is functioning normally.

An atrial sensing, ventricular inhibited pacemaker is a particular type of pulse generator, as further described in U.S. Pat. No. 3,648,707, that is coupled respectively by first and second leads to the atrium and ventricle of a patient's heart and is capable of sensing the beat rate of each of the patient's atrium and ventricle along its respective leads, whereby if a difference between the rates in excess of a predetermined limit is sensed, then the ASVIP pulse generator initiates generation of and application of delayed stimulating pulses to pace the patient's ventricle at the sensed beat rate of the atrium. The delay corresponds to the normal physiologic interval between atrial and ventricular contractions of the heart. A sequential pulse generator is somewhat similar to the ASVIP pulse generator, but further duplicates the natural activity in the heart in that the stimulating pulses first are applied to the patient's atrium along the first or atrial lead, with the ventricle stimulation being delayed and being applied after the noted delay by the ventricle or second lead at the rate of the atrium activity to the patient's ventricle.

In the above-discussed ASVIP-type and sequential-type pulse generators, it is critical that the connection of the first or atrial lead not be reversed with that of the second or ventricle lead, in that arrhythmias may be induced into the patient, which are potentially life-threatening. As an example of a possible arrhythmia resulting from the reversing of the interconnection of the ventricular and atrial connectors, the following hypothetical situation is readily contemplated. A patient with documented intermittant 3° A-V block and normal atrial rhythm receives an ASVIP pulse generator, the leads having been inadvertently reversed at the time of implantation of the device. Furthermore, at implantation the patient is in normal rhythm (i.e., atria and ventricles contract in sequence) within the normal operating rate range of the ASVIP pulse generator and the P-R (atrio-ventricular) delay is somewhat less than that of the artifical pacemaker. If we assume the ventricular amplifier (connected in this case to the atrium) senses the atrial signals, the ASVIP pulse generator will reset at each atrial contraction with no stimuli delivered to the heart, in this case the atria of the heart. The ventricular depolarizations will be of no consequence since the amplifier now connected to the ventricle will have been rendered refractory by the atrial depolarization sensed by the amplifier connected to the atria. It is important to note that on the surface EKG, no malfunction is observed since the atria and ventricles are beating rhythmically and in proper sequence. Now, if the patient suddenly experiences 3° A-V block with no intrinsic ventricular rate, the following sequence is likely to occur. The atria continue to contract rhythmically, their depolarization being sensed by the ventricular amplifier, resetting the stimulus output and rendering the other amplifier connected to the ventricles refractory. No stimuli are delivered to the heart with the result that there is no ventricular contraction. Of course, in most instances an idio-ventricular rate would exist, however, it is likely to be very slow and would continue unchecked. The patient, clearly, receives no therapeutic benefit from the ASVIP pulse generator and all the symptoms present prior to receiving the ASVIP pulse generator are permitted to continue. Other, more complex, potentially dangerous pacemaker induced arrhythmias are possible if inadvertent reversal of the atrial and ventricular leads should occur.

SUMMARY OF THE INVENTION

It is therefore an object of this invention to provide a new and improved set of first and second leads adapted to interconnect in a defined manner a pacemaker and tissue to be stimulated.

It is a more specific and primary object of this invention to provide a first or atrial, and a second or ventricle, leads adapted to interconnect a pulse generator of the ASVIP or sequential type, whereby the interchanging of the connections between the pacemaker and the first and second leads is prevented, thus preventing the induction of arrhythmias within and thus possible patient morbidity.

In accordance with these and other objects of the invention, there is provided a set of first or atrial, and second or ventricular leads, adapted to interconnect into corresponding first and second openings or bores of a pacemaker, to apply, respectively, stimulation to and to sense the heart activitiy of the patient's atrium and ventricle. Generally, the proximal end of each of the atrial and ventricular leads is configured to engage uniquely its corresponding first and second bores of the pacemaker to which it is to be electrically connected, to prevent the reversal of connection of the atrial and ventricle connectors therewith. In a particular illustrative embodiment of this invention, a portion of the atrial connector adjacent its proximal end is made of a reduced diameter with respect to its remaining portion and corresponding to a similar dimension or diameter of the atrial bore of the pacemaker, while a similar portion of the ventricular or second lead adjacent its proximal end is made of a larger dimension or diameter corresponding to that dimension or diameter of its ventricular bore through which it is connected to the pulse generator.

As a further aspect of this invention, each of the adjacent portions of the atrial and ventricular connectors is provided with a series of flexible rings disposed thereabout and adapted to seal with their corresponding first and second openings to help prevent the possible leakage of body fluids through the openings between the connector and its bores and into the circuitry of its pulse generator.

BRIEF DESCRIPTION OF THE DRAWINGS

These and other objects and advantages of the present invention will become more apparent by referring to the following detailed description and accompanying drawings, in which.

DETAILED DESCRIPTION OF THE PREFERRED EMBODIMENT

Figure 1:
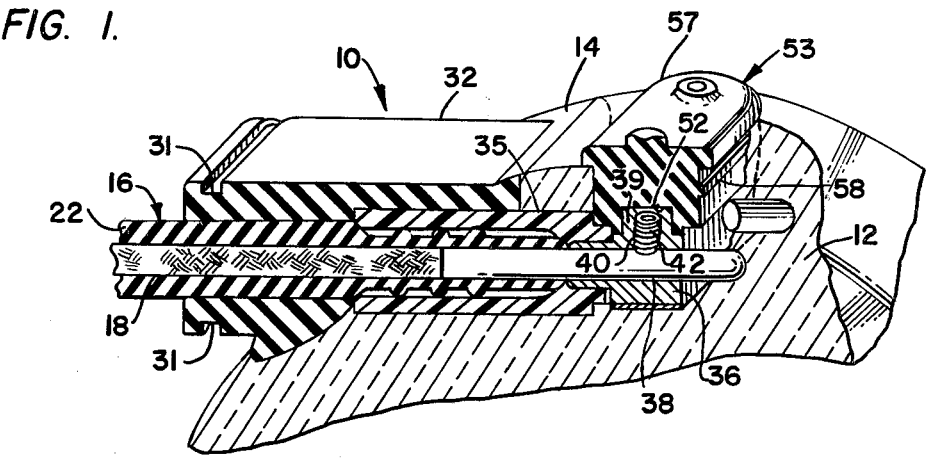
FIG. 1 is a cutaway pictorial view of a set of first and second connectors, and a pulse generator to which they are connected, in accordance with teachings of this invention.

Referring now to the drawings and in particular to FIG. 1, there is shown in partial perspective a sectioned view of a lead assembly in accordance with the teachings of this invention, to be connected with a tissue stimulating pulse generator 10, which, for example, comprises a cardiac pacemaker illustratively taking the form of the Medtronic Model 5993. Such a Medtronic pulse generator is an atrial sensing, ventricular inhibited (ASVIP) type pacemaker, which operates, as explained above, to sense the rate of contracting and expanding of the patient's atrium and ventricle, to measure the rate difference therebetween, and to initiate ventricle stimulation if the rate difference therebetween falls below a critical level. As indicated above, the pacemaker may also be of the sequential type.

The pulse generator 10 may comprise a battery power source and a miniaturized electrical circuit for sensing the atrial P-wave and the ventricular R-wave and for delivering electrical stimulating impulses at a preset pacing rate. The electrical components of the pulse generator 10 are encapsulated in a transparent epoxy resin encapsulent 12 that is compatible with and substantially inert to body fluids and tissue. This invention is more particularly directed to a set or pair of a first or atrial lead 16, and a second or ventricle lead 17, (see FIG. 2B) adapted to be connected, as will be explained in greater detail later, to the pulse generator 10.

Figure 2A:
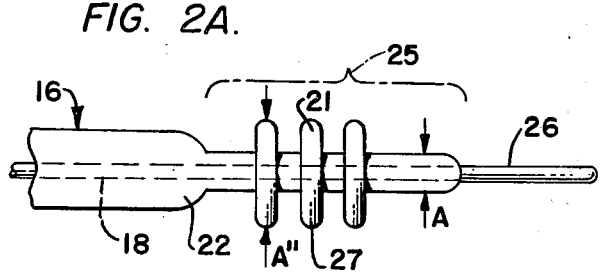
FIGS. 2A and 2B respectively show the first or atrial lead and the second or ventricular lead, as to be connected to the pulse generator as shown in FIG. 1.
Figure 2B:
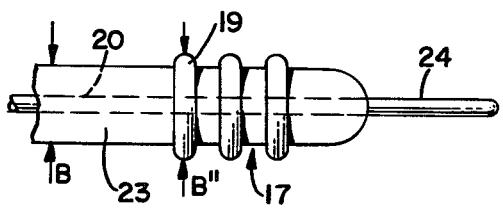

Referring to the leads 16 and 17, as shown in FIGS. 1, 2A and 2B, they comprise a pair of electrically conductive, tissue stimulating electrodes (not shown) at the distal ends, a corresponding pair of electrical conductors 18 and 20 electrically connected to the electrodes and electrically insulated from the surrounding body fluids and tissue by coverings 22 and 23 of silicone rubber, respectively. At the proximal ends of the conductors 18 and 20 are electrically conductive, terminal pins 26 and 24, respectively. As partially shown in FIG. 1 and more specifically shown in FIG. 2A, the first or atrial connector 16 includes a portion 25 adjacent the proximal end thereof and the terminal pin 26, of reduced diameter and having a plurality of sealing rings 27 disposed thereabout. Though not shown in FIG. 1 or the other drawings of this application, the first or atrial lead 16 may be illustratively of the type more specifically described in U.S. Pat. No. 3,939,843 of Smythe, and assigned to the assignee of this invention.

Figure 3A:
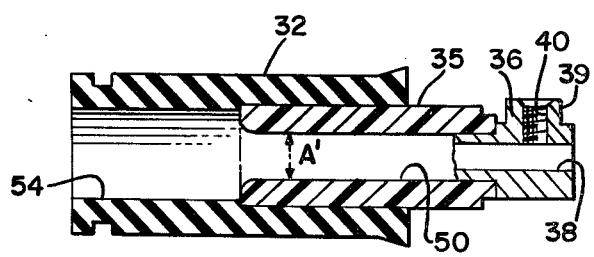
FIGS. 3A and 3B respectively show cross-sectioned views of the bores or openings of the pulse generator as shown in FIG. 1, into which the connectors of FIGS. 2A and 2B are to be inserted, respectively.
Figure 3B:
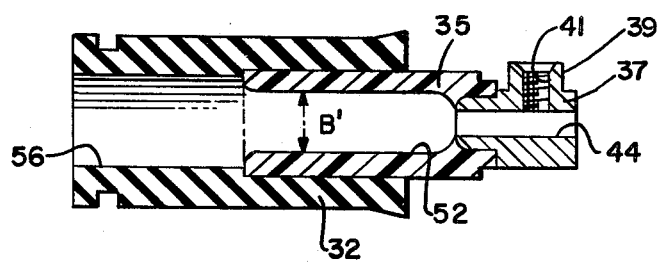

The pulse generator 10 as shown in FIG. 1 and in part in FIGS. 3A and 3B, comprises an elongated, silicone rubber boot 32 having openings 54 and 56 therein, with a groove 31 for receiving a nonabsorbable suture, the boot 32 projecting from the encapsulated pulse generator 10 and adapted to receive the proximal ends of the leads 16 and 17 comprising the terminal pins 26 and 24. The silicone rubber boot 32 cooperates with a connector sleeve 35, manufactured from a nonconductive hard plastic material and a pair of electrically conductive connector blocks 36 and 37 (see FIGS. 3A and 3B) that are adapted to be electrically connected to the electrical components of the pulse generator 10.

As shown in FIGS. 3A and 3B, the connector blocks 36 and 37 further comprise, respectively, a first set of bores or receptacles 38 and 44 for receiving the terminal pin of the leads and a second set of threaded bores 40 and 41 (only bore 40 is shown in FIG. 1) are adapted to receive a socket set screw 42. Situated between the connector blocks 36 and 37, and the external surface 14 of the encapsulent 12 is a silicone rubber grommet 53 which may be manufactured from implantable grade silicone rubber. The grommet 53 may be of one piece sufficiently long to cover and mate with both connector blocks 36 and 37, and set screws 42 of the depicted bipolar connector assembly. The grommet 53 consists of an external portion 57 contacting and protruding from the external surface 14 of the encapsulent 12 and an internal portion 58. The internal portion 58 is slipped over the upward projections 39 of the connector blocks 36 and 37. The grommet 53 provides a sterilizeable, electrically insulating, inert seal between the components comprising the socket set screws 42 and the connector blocks 36 and 37 and body fluids and tissue.

Referring now to FIGS. 2A and 2B, and 3A and 3B, the inventive aspect of the subject connector assembly will be described more fully in terms of the manner in which the interchangeability of the connection between the first and second leads 16 and 17 and the pulse generator 10 is prevented. First, with reference to FIGS. 2A and 2B, the first or atrial lead 16 is depicted as having a portion 25 adjacent its pin 26 of restricted diameter A, selected to permit insertion of the atrial connector 16 within both of the aligned openings 54 and 50 of the connector boot 32 and the connector sleeve 35, and also the openings 56 and 52 of the connector boot 32 and the connector sleeve 35. When both the atrial connector 16 and the ventricle connector 17 are inserted, the terminal pin 26 is permitted to be inserted within the bore 38 and electrical connection is made between the conductor 18, the terminal pin 26 and the connector block 36 to the pulse generating and sensing circuitry of the pulse generator 10. In particular, the proximal end of the atrial lead 16 is so configured and dimensioned to permit its insertion within both the bores as defined by the openings 54 and 50, and 56 and 52. In particular, the dimension A of the portion 25 is selected to correspond with dimension A', of the opening 50.

By contrast, the ventricle lead 17 is configured differently and its insulating covering 23 has a dimension B greater than dimension A of the reduced portion 25, that is particularly adapted to permit the insertion of the ventricle lead 17 only within openings 56 and 52, as shown in FIG. 3B, of the connector boot 32 and the connector sleeve 35. Thus, the configuration of the ventricle lead 17 and its dimensions ensure that it may be only inserted within the openings 56 and 52 to permit insertion of the terminal pin 24 within the bore 44 of the connector block 37, whereby its conductor 20 may be electrically connected through the terminal pin 24 and the conductor block 37 to a portion of the circuitry of the pulse generator 10 dedicated to the ventricle sensing and stimulation. However, as mentioned before, dimension B is selected to be greater than dimension A', whereby the insertion of the ventricle connector 17 is not permitted within the opening 50 associated with the atrial sensing and stimulating circuitry of the pulse generator 10. In an illustrative embodiment of this invention, dimension A is selected to be in the order of 0.142 inch, whereas dimension A' is set at 0.177 inch, thus permitting the insertion of the reduced portion 25 within the opening 50; by contrast, dimension B is determined to be 0.186 inch, thus preventing the insertion of the second, or ventricle lead 17 within the opening 50. In this regard, dimension B' is set to be 0.198 inch, thus permitting the insertion of the ventricle connector 17 within the openings 56 and 52. Thus, it may be understood that if during the surgical procedure during which the pulse generator 10 is implanted within the patient, the surgeon may inadvertently insert the first or atrial lead 16 within the openings 56 and 52 of the connector boot 32, and thereafter would attempt unsuccessfully to insert the ventricle connector 17 within the openings 54 and 50 through the connector boot 32, the surgeon would be prevented from so connecting the connector 17 and would be effectively warned to interchange and to correctly connect the first and second leads 16 and 17 to the pulse generator 10.

Further, the rings 27 and 19, respectively of the atrial and ventricle connectors 16 and 17, have substantially equal outside diameter dimensions A" and B," respectively, to permit the ready insertion within their corresponding openings and to help provide an effective seal therewith. Illustratively, dimension or diameter A" of the rings 27 is determined to be 0.206 inch, whereby an effective seal is effected within either opening 50 or 52, whereas the rings 19 are set to have a dimension B" of 0.206 inch to ensure an effective sealing within the opening 52.

As set out above, the first or atrial connector 16 may be inserted within either set of openings 56 and 52, or 54 and 50, but the second or ventricle connector 17 may be only inserted within openings 56 and 52, to make electrical contact to the ventricle portion of the pacemaker. It is critical that the ventricle and atrial connectors 16 and 17 not be reversed in their connection to the ASVIP pacemaker 10. However, it is contemplated that it may become desirable after the original implantation of the connectors 16 and 17 to remove the ASVIP pacemaker 10 and to substitute another pacemaker such as a ventricular demand-type pacemaker, and to make electrical connection to the already-implanted connector 17. To this end, the dimensions B and B" are selected to permit insertion of the ventricle connector 17 within a standard opening of such a ventricular-type pacemaker. Further, from the foregoing, it is apparent that the atrial connector 16 also could be inserted within the opening of a standard atrial demand or synchronous pacemaker, thus permitting the ready reconnection and substitution of a standard pacemaker, if that should become desirable. Further, it is noted that the outside diameters A" and B" of the rings 27 and 19 have been made, in an illustrative embodiment, to be substantially and nominally equal to provide sealing both with respect to the openings 50 and 52, as well as with respect to the openings of a standard pacemaker. It is contemplated that the rings 27 would be of a compressible material, e.g., silicone rubber, configured to fold back or be otherwise compressed as the atrial connector 16 is inserted within the opening 50, even though of a smaller diameter, permitting insertion of the atrial connector 16 therein.

In order to ensure proper sensing of the activity of the ventricle and atrium, as well as effective stimulation thereof, the impedance characteristics of, and in particular the leakage-to-surface impedance of the leads 16 and 17, is set as by appropriately designing its insulating materials and dimensions to ensure a minimum leakage-to-surface impedance of a value of approximately 50 Kohms.

Numerous changes may be made in the above-described apparatus and the different embodiments of the invention may be made without departing from the spirit thereof; therefore, it is intended that all matter contained in the foregoing description and in the accompanying drawings shall be interpreted as illustrative and not in a limiting sense.

What is claimed is:

1. A set of first and second body-implantable discrete leads adapted to electrically interconnect first and second body tissues and a source of electrical energy, wherein the improvement comprises:
    (a) first and second conductors of said first and second leads, respectively;
    (b) first and second insulating means encapsulating and electrically insulating, respectively, said first and second leads and each being of a material which is substantially inert to body fluids and tissue;
    (c) first and second discrete electrode means connected, respectively, to said first and second leads; and
    (d) first and second contact means associated with the source of electrical energy, and including first and second means associated with said first and second leads respectively for ensuring that said second electrode means may only be electrically engaged to the source of electrical energy through said second contact means.

2. The body-implantable leads as claimed in claim 1, wherein said ensuring means comprises first and second means for defining an opening for receiving, respectively, said first and second leads, said first and second openings being configured differently to both receive said first lead and to prevent the insertion of said second lead into said first opening.

3. The body-implantable leads as claimed in claim 2, wherein said first and second openings have, respectively, first and second dimensions corresponding to third and fourth dimensions of said first and second insulating means, permitting insertion thereof within said first and second openings, respectively, said first dimension being less than said second dimension to prevent the insertion of said second lead within said first opening.

4. The body-implantable leads as claimed in claim 1, wherein each of said first and second leads includes first and second sealing means, respectively, disposed about said first and second insulating means to ensure a sealing relationship with said first and second openings.

5. The body-implantable leads as claimed in claim 4, wherein said first and second leads includes first and second sealing rings, respectively, disposed about said first and second insulating means and having nominally equivalent outside diameters, said sealing rings being of a resilient material and adapted, on said first lead, to be compressed to said first dimension when said first connector member is inserted into said first opening and to said second dimension when said first connector member is inserted into said second opening.

6. In a pacemaker comprising a set of first and second body-implanted leads adapted to electrically interconnect, respectively, the atrium and ventricle of a patient's heart, and a pulse generator adapted to uniquely stimulate the atrium and ventricle of a heart of a patient into which said pulse generator is implanted, wherein the improvement in the set of first and second discrete body-implanted leads and said pulse generator comprise:
(a) first and second conductors associated, respectively, with said first and second leads;
(b) first and second insulating coverings encapsulating and electrically insulating, respectively, said first and second leads and each being made of a material which is substantially inert to body fluids and tissue;
(c) first and second electrodes connected, respectively, to said first and second conductors;
(d) first and second connector members connected, respectively, to said first and second conductors;
(e) first and second discrete contact means associated, respectively, with the distinct atrial and ventricle stimulating portions of said pulse generator ; and
(f) first means for defining first and second openings for receiving, respectively, said first and second connector members, said first and second openings having different configurations to both receive said first connector member, but to inhibit the insertion of said second connector member into said first opening.

7. The body-implantable leads as claimed in claim 6, wherein said first and second openings have, respectively, first and second dimensions corresponding to third and fourth dimensions of said first and second insulating coverings of said first and second connector members, permitting insertion thereof within said first and second openings, respectively, said first dimension being less than said second dimension to prevent the insertion of said second connector member within said first opening.

8. The body-implantable leads as claimed in claim 6, wherein each of said first and second leads includes first and second sealing rings, respectively, disposed about said first and second insulating means to help ensure a sealing relationship with said first and second openings.

9. The body-implantable leads as claimed in claim 8, wherein said first and second openings have, respectively, first and second dimensions corresponding to third and fourth dimensions of said first and second insulating coverings of said first and second connector members, and said first and second sealing rings respectively have nominally equivalent outside diameters, said aforementioned third and fourth dimensions being selected to permit the insertion of said first connector member into said first and second openings, but to inhibit the insertion of said second connector member into said first opening.

10. The body-implantable leads as claimed in claim 6, wherein said first and second leads include first and second sealing rings, respectively, disposed about said first and second insulating means and having nominally equivalent outside diameters, said sealing rings being of a resilient material and adapted, on said first lead, to be compressed to said first dimension when said first connector member is inserted into said first opening and to said second dimension when said first connector member is inserted into said second opening whereby said sealing rings of said first lead effect a sealing relationship with either of said first and second openings.

11. The body-implantable leads as claimed in claim 6, wherein said ensuring means permits said first connector member to be electrically engaged to said ventricle portion through said second contact means, but inhibiting the electrical engagement between said second connector member and said atrial portion through said first contact means.

12. A set of first and second body-implantable, discrete leads adapted to be electrically interconnected respectively to the atrium and ventricle of a patient's heart, and to either of a first pulse generator adapted to stimulate or sense electrical signals of the atrium and ventricle of the heart of a patient, or to a second standard type pulse generator, said first pulse generator having first and second contact means, associated respectively with the distinct atrium and ventricle stimulating portions of said first pulse generator and including first means for defining first and second openings, said second standard type pulse generator having second means for defining third and fourth openings, said first and second body implantable leads comprising:
(a) first and second discrete conductors associated respectively, with said first and second leads;
(b) first and second insulating coverings encapsulating and electrically insulating, respectively, said first and second leads and each being made of a material which is substantially inert to body fluids and tissue;
(c) first and second electrodes connected, respectively, to said first and second conductors;
(d) first and second discrete connection members connected, respectively, to said first and second conductors; and
(e) said first and second connector members having different configurations to inhibit insertion of said second connector member into said first opening, while permitting said first and second connector members to be inserted within either of said third or fourth openings.

13. The set of leads as claimed in claim 12, wherein said first and second openings have, respectively, first and second dimensions corresponding to third and fourth dimensions of said first and second insulating covering of said first and second connector members, said first dimension being less than said second dimension to prevent the insertion of said second connector member within said first opening.

14. The set of leads as claimed in claim 13, wherein said third and fourth openings have a dimension not less than said second dimension to permit the insertion of the first connector member into each of either of said first and second connector members.

15. The set of leads as claimed in claim 13, wherein said first and second leads include first and second sealing rings, respectively, disposed about said first and second insulating means and having nominally equivalent outside diameters, said sealing rings being of a resilient material and adapted, on said first lead, to be compressed to said first dimension when said first connector member is inserted into said first opening and to said second dimension when said first connector member is inserted into said second opening.

* * * * *